United States Patent [19]

Jorgensen

[11] 4,155,870

[45] May 22, 1979

[54] SKIN CLEANING COMPOSITIONS CONTAINING WATER-INSOLUBLE GLASS BUBBLES

[75] Inventor: Jens L. Jorgensen, Ham Lake, Minn.

[73] Assignee: Minnesota Mining and Manufacturing Company, Saint Paul, Minn.

[21] Appl. No.: 789,666

[22] Filed: Apr. 21, 1977

Related U.S. Application Data

[63] Continuation-in-part of Ser. No. 678,413, Apr. 19, 1976, abandoned.

[51] Int. Cl.² .................. C11D 9/20; C11D 9/18; C11D 3/14; C11D 3/12
[52] U.S. Cl. ............................ 252/131; 252/89 R; 252/DIG. 5
[58] Field of Search ............... 252/131, 128, 134, 90, 252/DIG. 5, 89 R

[56] References Cited

U.S. PATENT DOCUMENTS

| | | | |
|---|---|---|---|
| 2,038,653 | 4/1936 | Gilbert | 252/131 X |
| 2,945,815 | 7/1960 | Diaz | 252/131 X |
| 3,281,367 | 10/1966 | Jones et al. | 252/DIG. 14 X |
| 3,408,299 | 10/1968 | Henry | 252/134 X |
| 3,645,904 | 2/1972 | Beach | 252/DIG. 5 X |

FOREIGN PATENT DOCUMENTS 1429911 3/1976 United Kingdom.

*Primary Examiner*—Harris A. Pitlick
*Attorney, Agent, or Firm*—Cruzan Alexander; Donald M. Sell; Carolyn A. Bates

[57] ABSTRACT

Skin cleaning compositions are disclosed comprising a conventional skin cleaning base having incorporated therein 0.3 to 32 percent by weight of water-insoluble glass bubbles. The glass bubbles aid in cleaning and removing stains from the skin without imparting abrasive feel.

10 Claims, No Drawings

SKIN CLEANING COMPOSITIONS CONTAINING WATER-INSOLUBLE GLASS BUBBLES

This is a continuation-in-part of application Ser. No. 678,413 filed Apr. 19, 1976, now abandoned.

This invention relates to skin cleaning compositions having scrubbing aids incorporated therein to enhance the removal of dirt and stains from the skin. The invention relates particularly to skin cleaning compositions of the cream and lotion type and to bar soap compositions. However, powdered and granular soap compositions are also included within the scope of the invention.

Skin cleaning compositions having abrasive particles incorporated therein as scrubbing aids are well known in the art. U.S. Pat. No. 2,494,827 discloses abrasive detergent compositions containing water-insoluble phosphates which may serve the dual purpose of providing scrubbing aids and softening water. In addition to water insoluble phosphates, these detergent compositions may contain scrubbing aids such as cornmeal, volcanic ash, pumice, diatomaceous earth and wood dust.

U.S. Pat. No. 2,610,153 discloses a skin cleaning composition wherein the mild abrasive is a chemically treated residue obtained as a byproduct in soybean processing. Particles of the residue ground to pass through a 20 mesh screen or finer are suggested for incorporation into the skin cleaning compositions.

A therapeutic method for the abrasion of human skin is disclosed in U.S. Pat. No. 3,092,111. This method is for the treatment of acne and comprises repeatedly rubbing the skin with an abrasive composition having the characteristics of a paste and comprising a non-oleaginous detergent base having dispersed therein an inorganic abrasive which has a hardness greater than 7 as measured by Moh's index. The inorganic abrasive is non-piezoelectric and has a particle size distribution between 125 and 710 microns. The composition is designed to create desquamation, and the inorganic abrasive particles have sharp corners to gouge the skin sufficiently to dig out the keratinous plugs from the hair follicles. The preferred abrasive for use in the composition is aluminum oxide particles.

U.S. Pat. No. 3,645,904 discloses a skin cleaning composition having plastic synthetic resin particles in the size range of 74 to 420 microns incorporated therein as scrubbing aids. Examples of suitable plastic particles include "microballoons" made from phenolic resin, urea formaldehyde or polystyrene. Plastic resin particles are described as imparting moderate but persistent scrubbing action to the cleaner without imparting a coarse, unpleasant feel.

Cleaning compositions containing solid inorganic particles which have been "spherulitized" to reduce abrasion are disclosed in U.S. Pat. No. 2,038,653. Although these compositions are primarily intended for cleaning hard surfaces such as window glass and porcelain fixtures, it is suggested that solid spherical particles may be advantageous in skin cleaning compositions such as mechanic's soaps.

While skin cleaning compositions of the prior art containing particulate scrubbing aids have been somewhat beneficial in removing dirt and stains from skin, they generally suffer from the disadvantage of having an unpleasant abrasive feel and many cause irritation with prolonged scrubbing. The problem is particularly associated with inorganic particles which are irregularly shaped and have sharp points and corners. Organic particles used in skin cleaners are also somewhat abrasive feeling since the grinding process which is used to reduce them to the desired size produces irregularly shaped particles. Organic particles are also generally soft and resilient, and as a result, they are less effective scrubbing aids. An additional disadvantage associated with organic particles is their tendency to agglomerate during use which increases their abrasive feel.

Skin cleaning compositions containing solid spherical inorganic particles such as glass beads are somewhat effective in overcoming the disadvantages associated with most prior art compositions. However, glass beads settle very rapidly in water because of their high specific gravity. Prolonged use can cause build-up of glass beads in sewer lines and drain-traps, leading to clogged pipes. Additionally, glass beads present significant formulation problems. Because of their density, they are difficult to suspend in lotion-based compositions. In bar soaps, they impart an undesirable grey color, and the bars are rather heavy.

The present invention overcomes many of the problems associated with prior art skin cleaners by providing skin cleaning compositions having glass bubbles incorporated therein. Glass bubbles are smooth and non-abrasive feeling. They are low in density and float in water, thus being easy to formulate and rinse away with water. Surprisingly, compositions of the invention have improved cleaning and stain removing properties over more abrasive skin cleaners and over skin cleaners containing solid spherical particles such as glass beads.

In accordance with the present invention there is provided a skin cleaning composition comprising a conventional skin cleaning base having incorporated therein 0.3 to 32 percent by weight of glass bubbles in the size range of 20 to 200 microns.

The term "conventional skin cleaning base" as used herein means those bases substantially free of water insoluble particulate material. The preferred conventional skin cleaning bases for use in the invention are those of the so called "waterless" type such as creams or lotions which clean without the use of water. Bar soap compositions are also preferred. Dry or granulated soap compositions are also suitable conventional skin cleaning bases according to the invention.

The skin cleaning compositions of the present invention are non-abrasive feeling and pleasant to use. The glass bubbles do not agglomerate during use and the compositions retain their non-abrasive feel throughout the cleaning process. The skin cleaning compositions of the invention are effective in removing grease, inks, dyes, paint, varnishes and other "hard to remove" substances from skin.

It is believed that the skin cleaning compositions of the invention derive their improved properties from the shape, hardness, and low density of the glass bubbles incorporated therein. Due to their spherical shape, the glass bubbles rotate when rubbed on the skin and roll out stains from the cracks and crevices in the skin surface. In addition to enhancing cleaning, the glass bubbles are not abrasive and do not cause skin irritation. The low density of the glass bubbles allows them to be incorporated into the base in relatively large quantities without measurably affecting the weight of the composition. Since they float in water, they are easily rinsed away and do not build up in drain pipes. Glass bubbles having a density in the range of 0.1 to 0.5 g/cc when tested in accordance with ASTM D 2840-69 are preferred for use in the compositions of the invention. However, bubbles having a density as low as 0.05 and as high as about 1.0 may be used.

The glass bubbles incorporated into the compositions of the invention must be water-insoluble and sufficiently strong to withstand crushing from normal pressure applied during skin cleansing. Glass bubbles having a crush strength (10% collapse in glycerol) of 250 psi or greater are generally suitable. In the case of bar soaps which are subjected to high pressure during manufacture, glass bubbles having a crush strength greater than 1000 psi are recommended.

The glass bubbles may range in size from 20 to 200 microns. The preferred size for minimum abrasive feel is an average of about 50 microns with the largest average size being about 80 microns. Glass bubbles larger than 200 microns clean equally well, but feel more abrasive. Those less than 20 microns are too small to improve the cleaning properties of the base.

The amount by weight and volume of glass bubbles incorporated into the skin cleaning base will vary depending upon the type of base used. Generally, levels as low as 0.3 percent and as high as 32 percent by weight of the composition may be used. Compositions containing less than 0.3 percent by weight of glass bubbles do not measurably enhance the cleaning ability of the base. Compositions containing 33 percent or more by weight of glass bubbles are too viscous. In a lotion or cream base, 1 to 7 percent by weight of glass bubbles provide cleaning with minimum abrasive feel. At this loading, the overall cost of the composition is not significantly increased. In bar soaps the preferred loading of glass beads is about 2 to 12 percent by weight. Soap bars prepared according to the invention have the desirable feature of floating in water.

The preferred conventional skin cleaning base for the compositions of the invention is a water-in-oil emulsion. This emulsion is preferred because the continuous phase is the oil phase, and a minimum amount of rubbing is necessary to initiate cleaning action to remove stains. An oil-in-water emulsion is also suitable, however, more rubbing is required to initiate stain removal.

The cleaning base normally contains one or more solvents having a low KB value such as isoparaffin solvents or deodorized kerosenes. Stronger solvents such as toluene may be included in the compositions to remove tougher stains. However, toluene is harsher to the skin as well as more toxic than the preferred solvents. Cleaning bases which do not contain solvents, e.g., cold cream bases, may be used to remove makeup and less stubborn stains. Other ingredients commonly included in lotion or cream skin cleaners include emollients such as mineral oil and lanolin, surfactants, thickeners, colorants, perfumes, preservatives, etc.

Stains which are readily removed from hands with the skin cleaning compositions of the invention include tar, oils, grease, paint, varnish, dirt and rust. These stains may be removed faster if the stain is not too dry. Dried stains may be removed, but more rubbing is necessary because the solvents used in the compositions generally have a low KB value.

The cleaning and stain-removing ability of skin cleaning compositions is difficult to evaluate quantitatively. However, a laboratory test has been devised to evaluate the stain removing ability of different skin cleaners of the cream or lotion type. This test can also be used to determine the effect of various cleaning bases as well as the concentration of glass bubbles to be used for optimum results.

It has been found that a numerical value (cleaning value) can be obtained for each skin cleaning composition tested. The cleaning value (CV) of a skin cleaner may be defined as the amount of work necessary to remove a specific stain from a substrate. This value is the number of revolutions of a rotating brush necessary to remove a stain from a flat surface under constant conditions.

According to the test procedure, the stain to be removed is applied with a 3½ mil (0.088 mm) draw-down bar on a flexible uncured rubber substrate. This rubber substrate is normally used for sand blasting granite and is referred to as "SCOTCH" Brand Sand Blast Stencil Tape #507-45BC Buttercut with a pressure-sensitive adhesive and release liner applied to one surface, (available from 3M Company, St. Paul, Minn.). This substrate is used because it is flat and flexible and has surface properties similar to human skin. The adhesive coating on one surface holds the substrate firmly in place during the test.

Various stains may be used, depending on the type of cleaning base and the intended use of the test composition. When compositions containing a solvent were tested the stain utilized was a rubber-modified, asphaltic-based crack filler (G & H Black Top Crack Fix, Gibson-Homans Co., Cleveland, Ohio). This stain is very difficult to remove from the hands with conventional hand cleaners. The stain is applied to the non-adhesive surface of the substrate and allowed to dry overnight so that the stain is completely and uniformly dry.

The stain removal device consists of a stiff plastic brush powered by an air motor. The brush is circular and has a diameter of 84 cm with bristles covering approximately 1.8 cm of the outer perimeter. The bristles are made of polypropylene and are approximately 2.4 cm in length, and each individual bristles is about 0.18 mm in diameter.

A counter is attached to the brush so that the number of revolutions of the brush may be recorded. The rubber substrate with the dried stain is applied to a laboratory jack and held firmly in place by the pressure-sensitive adhesive covering the lower surface of the substrate. Eight milliliters of the test composition are applied to the area of the stain to be removed. The laboratory jack with the rubber substrate attached is raised sufficiently high so that it contacts the brush with a uniform and constant pressure. (i.e., sufficient to touch but not bend the bristles). It has been found that results are more reproducible if the support to which the brush is attached is firmly anchored to a solid base so that uniform pressure is applied to the bristles throughout the experiment. In the early tests performed with the apparatus, the support to which the brush was attached was not firmly anchored and weights were applied to the brush to insure complete contact with the stain. This resulted in the cleaning values being somewhat lower than values obtained when the brush is firmly anchored.

The brush is allowed to rotate 60 times per minute. The rotating brush is stopped every 15 seconds so that the substrate can be inspected to determine when the stain is removed. The number of revolutions necessary to remove the stain completely is called the cleaning value (CV).

When a series of skin cleaning compositions are being evaluated, the rotating brush must be cleaned in solvent and dried between usage. This is to prevent particulate and vehicle contamination of the brushes which may result in erroneous cleaning values.

This method provides a means for comparing the stain-removing ability of various skin cleaning compositions. Actual stain removal from the hands and arms with skin cleaning compositions correlates well with the cleaning value obtained for the same compositions in the laboratory method described above. When tested on skin each composition was given a rating of poor, fair, good or excellent, instead of a numerical value.

As noted above, cleaning values are influenced somewhat by the amount of glass bubbles incorporated into a skin cleaning base as well as the type of base used. Although the cleaning values for various bases differ greatly, the addition of glass bubbles improves the cleaning value of each base tested.

The following non-limiting examples illustrate the skin cleaning compositions of the invention.

EXAMPLE 1

Oil-in-Water Cleansing Cream (No Solvent)

A skin cleaning compositions was prepared with the following ingredients:

| Ingredient | | Parts by Weight |
|---|---|---|
| A | Mineral oil (70 SSU) | 23.75 |
|   | Cetyl Alcohol | 1.90 |
|   | Lanolin | 1.90 |
|   | Glycerol Monostearate (SE) | 9.50 |
|   | Polysorbate 60 | .95 |
|   | Glycerine | 5.70 |
| B | Deionized Water | 51.30 |
| C | Glass bubbles, 90% by volume being in the size range of 20-95 microns (3M Brand B-38-4000, 3M Co., St. Paul, Minn.) | 5.00 |
|   |   | 100.00 |

The ingredients of Part A were mixed together and heated to 70°-75° C. The distilled water of Part B was heated to 75° C. and added slowly, while stirring at high speed, to Part A. The glass bubbles of Part C was then added with mixing until the bubbles were uniformly dispersed.

EXAMPLE 2

Oil-in-Water Cold Cream

Using the procedure of Example 1, a cold cream composition was prepared with the following ingredients:

| Ingredient | | Parts by Weight |
|---|---|---|
| A | Mineral Oil (70 SSU) | 38.00 |
|   | Petrolatum | 2.85 |
|   | Beeswax | 6.65 |
|   | Cetyl Alcohol | 1.90 |
|   | Stearyl Alcohol | 1.90 |
|   | Polyoxyethylene 20 Sorbitan Beeswax Derivative | 5.70 |
|   | Polyoxyethylene 20 Sorbitan Monopalmitate | 3.80 |
| B | D.I. Water | 38.20 |
| C | Glass bubbles, 90% by volume in size range of 20-95 microns. (3M Brand B-38 4000) | 1.00 |
|   |   | 100.00 |

EXAMPLE 3

Water-in-Oil Skin Cleaning Composition

Using the procedure of Example 1, a skin cleaning composition was prepared with the following ingredients:

| Ingredient | | Parts by Weight |
|---|---|---|
| A | Isoparaffin Solvent | 24.50 |
|   | Mineral Oil (350 SSU) | 7.00 |
|   | Petrolatum | 3.50 |
|   | Paraffin Wax (m.p. 59-60° C.) | 7.00 |
|   | Aluminum Stearate | 2.00 |
|   | Sorbitan Sesquioleate | 5.00 |
|   | Sorbitan Trioleate | 1.00 |
|   | Propyl Paraben | .10 |
| B | Water | 44.70 |
|   | Methyl Paraben | .20 |
| C | Glass bubbles, 90% by volume in size range of 20-95 microns (3M Brand B-38-4000) | 5.00 |
|   |   | 100.00 |

EXAMPLE 4

Water-in-Oil Skin Cleaning Composition

A skin cleaning composition was prepared with the following ingredients:

| Ingredient | | Parts by Weight |
|---|---|---|
| A | Magnesium aluminum silicate | 2.50 |
|   | Water | 30.00 |
|   | Sorbitan Monostearate | 2.00 |
| B | Polyoxyethylene 20 Sorbitan Monostearate | 8.00 |
|   | Deodorized kerosene | 35.00 |
|   | Methylcellulose, 4000 cps | 0.50 |
| C | Water | 17.00 |
|   | Preservative | q.s. |
| D | Glass bubbles, 90% by volume in size range of 20-160 microns. (3M Brand B-23-500) | 5.00 |
|   |   | 100.00 |

In Part A, the magnesium aluminum silicate was added slowly to the water and agitated continuously until the mixture was smooth (about one hour). Part A was then heated to 62° C. The ingredients of Part B were mixed together, heated to 60° C. and added to heated Part A. The mixture was stirred until cool. In Part C, 10 ml of water were heated to 90° C., methylcellulose was added very slowly and mixed thoroughly until dispersed. The remainder of the water was added, the mixture cooled and added, with mixing, to the emulsion of Parts A and B. The bubbles of Part D were added and mixed until dispersed.

EXAMPLE 5

Bar Soap composition

A bar soap was prepared with the following ingredients:

| Ingredient | Parts by Weight |
|---|---|
| Distilled Tallow Fatty Acid | 37.60 |
| Distilled Coconut Fatty Acid | 16.30 |
| Caustic Soda 36% (40.7 Baume) | 26.40 |
| Water | 4.70 |
| Perfume | q.s. |

| Ingredient | Parts by Weight |
|---|---|
| Glass bubbles, 90% by volume in size range of 20–160 microns (3M Brand B-23-500) | 15.00 |
| | 100.00 |

The ingredients were mixed together in the order listed, heated to 82° C. and mixed until smooth. The mixture was cast into molds and allowed to harden.

The bar soap was used to clean hands soiled with factory grease. It was found to clean significantly better than a bar of soap of similar composition without glass bubbles.

To show the improved cleaning ability of the compositions of the invention over compositions containing solid spherical glass particles, comparative tests were performed using the test method described hereinabove. Comparisons were made on a volume basis as opposed to a weight basis because of the large difference in density between glass bubbles and glass beads. When a composition containing glass bubbles was compared with a composition containing an equal volume of glass beads, equal numbers of spheres or scrubbing aids were present in each composition, and valid comparisons could be made.

The same skin cleaning base was used throughout the comparative tests. The base contained the following ingredients in the relative amounts shown:

Base Formulation

| | Ingredient | Amount |
|---|---|---|
| A | Isoparaffin solvent | 25.80 |
| | Mineral oil (350 SSU) | 7.40 |
| | Petrolatum | 3.70 |
| | Paraffin wax (MP 59–60° C.) | 7.40 |
| | Aluminum stearate | 2.10 |
| | Sorbitan Sesquioleate | 5.25 |
| | Sorbitan Trioleate | 1.05 |
| | Propyl Paraben | .10 |
| B | Water | 47.00 |
| | Methyl Paraben | .20 |
| | | 100.00 |

In compositions containing glass bubbles, 90% by volume of the bubbles were in the size range of 20–95 microns (3M Brand B-38-4000). When glass beads were used, they were in the size range of 105–53 microns (Potters Industries 2429).

In each test, 8 milliliters of the test composition was used. The results of the tests are shown in the following table:

COMPARISON OF GLASS BUBBLES AND GLASS BEADS IN SKIN CLEANING COMPOSITIONS

| Glass Bubbles | | | Glass Beads | | |
|---|---|---|---|---|---|
| Volume % | Wt. % | Cleaning Value | Volume % | Wt. % | Cleaning Value |
| 22.6 | 10.0 | 687 | 22.6 | 42.0 | 1059 |
| 9.5 | 3.8 | 868 | 9.5 | 20.7 | 1214 |
| 20.8 | 9.0 | 690 | 20.9 | 39.5 | 1211 |
| 34.5 | 16.7 | 591 | 34.5 | 56.7 | 1357 |
| 44.1 | 23.0 | 912 | 44.2 | 66.3 | 1129 |
| 51.3 | 28.6 | 738 | 51.3 | 72.3 | 1265 |
| 61.2 | 37.5 | Too stiff over 2000 | 61.3 | 79.7 | Two stiff over 2000 |
| Base | — | 1610 | 43.0 | 65.2 | 1212 |
| 1.29 | .5 | 890 | | | |
| 58.7 | 35.0 | Very stiff over 2000 | | | |
| 55.3 | 32.0 | 1247 | | | |
| .52 | .2 | 1647 | | | |
| .79 | .3 | 1343 | | | |
| .99 | .4 | 999 | | | |

The data indicate that compositions containing glass bubbles remove stains better than compositions containing an equivalent volume of glass beads. Both glass bubbles and glass beads improve the cleaning ability of the base itself, but glass bubbles provide a substantially greater improvement. Compositions containing as low as 0.3 percent by weight of glass bubbles and as high as about 32 percent, show improvement over the base.

Soap bars made according to the invention could not be evaluated using the cleaning test described hereinabove. It was determined that the most effective method of determining the stain removal properties of bar soaps was a paired hand washing comparison stain removal test. The test procedure is as follows:

1. Wash hands thoroughly with soap and water. Towel dry.
2. Let hands air dry for 3 minutes.
3. Apply one gram of stain (asphaltic based patching compound made by Gibson Homens Co. called Handi-Patch #6280 thinned with 10% heptane.) to palm of each hand and rub hands together thoroughly to assure even distribution of soil over palms of hands.
4. Let hands dry for 3 minutes or until no longer tacky.
5. Place plastic glove on one hand.
6. Rub hands together rapidly for 15 seconds under lukewarm running water to set the stain on the hand to be cleaned.
7. Take the test soap bar and wash the test hand for 20 seconds by running the bar over the soiled areas.
8. Put the soap bar down and continue washing for 25 seconds using the generated lather.
9. Rinse hand and repeat steps 7 and 8 two additional times.
10. Remove plastic glove and place another glove over cleaned hand and repeat steps 6, 7, 8, and 9.
11. Have percent soil removal read by observers and record.

Using the hand washing test, soap bars made with a standard 82/18 tallow coconut fatty acid base were able to remove an average of 43% of the standard stain from the hands. A soap bar using the same base with 7% glass bubbles added removed 62% of the stain. This indicates the addition of glass bubbles enhances stain removal of soap bars. These bars also did not feel abrasive.

Two examples of soap bars made with glass bubbles according to the invention are as follows:

EXAMPLE 6

| Water | 13.0% |
|---|---|
| Perfume | 1.5% |
| 82/18 tallow-Coconut Soap Base | 78.0% |
| 50 micron glass bubbles (B-38-4000, available from 3M Company, St. Paul, Minn.) | 7.5% |
| | 100.0% |

The perfume and water were blended into the soap base using conventional soap manufacturing procedures. The glass bubbles were blended in the plodder, followed by extrusion into soap bars.

EXAMPLE 7

| Cold-made frame soap bar | |
|---|---|
| Sodium coconut soap base | 73.0% |
| Water | 22.0% |
| 50 micron glass bubbles (B-38-4000 available from 3M Company, St. Paul, Minn.) | 5.0% |
| | 100.0% |

Soap bars were made in accordance with the procedure of Example 5, except the bars were stamped out on a press.

Glass bubbles having a crush strength of 500 psi or less tend to be crushed during the commercial manufacture of soap bars and should be avoided when high pressure manufacture is involved.

What is claimed is:

1. A skin cleaning composition comprising a conventional skin cleaning base having incorporated therein from 0.3 to 32 percent by weight of water-insoluble glass bubbles having an average size of at least 50 microns.

2. A skin cleaning composition comprising a conventional water-in-oil emulsion having incorporated therein from 0.3 to 32 percent by weight of water-insoluble glass bubbles in the size range of 20 to 200 microns.

3. The composition according to claim 1 wherein the glass bubbles comprise 1 to 7 percent by weight of said composition.

4. The composition according to claim 1 wherein said glass bubbles have an average size of 50 to 80 microns.

5. A skin cleaning composition comprising a conventional bar soap base having incorporated therein from 0.3 to 32 percent by weight of water-insoluble glass bubbles in the size range of 20 to 200 microns.

6. The composition according to claim 5 wherein the particles comprise 2 to 12 percent by weight of the composition.

7. A skin cleaning composition comprising a conventional oil-in-water emulsion skin cleaning base having incorporated therein glass bubbles in the size range of 20 to 90 microns in an amount comprising from 1 to 7 percent by weight of said composition.

8. A method of removing stains from human skin comprising rubbing the skin with an effective amount of a skin cleaning composition comprising a conventional skin cleaning base having incorporated therein from 0.3 to 32 percent by weight of water-insoluble glass bubbles in the size range of 20 to 200 microns.

9. The method of claim 8 wherein the skin cleaning base is a water-in-oil emulsion.

10. The method of claim 8 wherein the skin cleaning base is a bar soap.

* * * * *